US006961611B2

United States Patent
Dupelle

(10) Patent No.: US 6,961,611 B2
(45) Date of Patent: Nov. 1, 2005

(54) MULTI-CONFIGURATION DEFIBRILLATION CONNECTOR

(75) Inventor: Michael R. Dupelle, N. Attleboro, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 181 days.

(21) Appl. No.: 10/608,861

(22) Filed: Jun. 27, 2003

(65) Prior Publication Data

US 2004/0267323 A1 Dec. 30, 2004

(51) Int. Cl.[7] ............................................. A61N 1/365
(52) U.S. Cl. ........................................................ 607/5
(58) Field of Search ................................ 607/5, 36–38, 607/142

(56) References Cited

U.S. PATENT DOCUMENTS

| | | | | |
|---|---|---|---|---|
| 5,411,528 A | * | 5/1995 | Miller et al. | 607/5 |
| 2004/0034393 A1 | * | 2/2004 | Hansen et al. | 607/37 |

* cited by examiner

Primary Examiner—George Manuel
(74) Attorney, Agent, or Firm—Fish & Richardson P.C.

(57) ABSTRACT

A multi-configuration electrical connector for use in making electrical connections between an external defibrillator and defibrillation electrodes applied to a patient. The multi-configuration connector comprises a connector body; at least first and second pairs of electrical terminal elements supported in the connector body; and a pair of electrical conductors within the connector body, each conductor of the pair being configured to be electrically connected to one of the electrical terminal elements in each of the first and second pairs of electrical terminal elements, wherein the connector body and first and second pairs of electrical terminal elements are configured so that the multi-configuration connector is able to mate alternatively with first and second mating defibrillation electrode connectors, with the first pair of electrical terminal elements in electrical contact with mating electrical elements of the first mating defibrillation connector when the multi-configuration connector is mated with the first mating defibrillation connector, and with the second pair of electrical terminal elements in electrical contact with mating electrical elements of the second mating defibrillation connector when the multi-configuration connector is mated with the second mating defibrillation connector.

11 Claims, 4 Drawing Sheets

MULTI-CONFIGURATION DEFIBRILLATION CONNECTOR

TECHNICAL FIELD

This invention relates to connectors for connecting external defibrillation electrodes to defibrillators.

BACKGROUND

An external defibrillator delivers a defibrillation pulse to a patient through a pair of chest electrodes (FIGS. 1 and 2). The electrodes are connected to the defibrillator by a cable, which is typically divided into two parts, a patient cable, with a wire extending from each electrode to a patient connector, and a defibrillator cable extending from the defibrillator to a defibrillator connector that mates with the patient connector. Typically, each defibrillator manufacturer uses electrical connectors with configurations unique to that manufacturer, with the result that one manufacturer's electrodes cannot typically be connected to another manufacturer's defibrillator.

SUMMARY

We have discovered that a practical solution to the problem of incompatible defibrillation connectors is to provide a multi-configuration electrical connector capable of mating with connectors of different configurations. The invention avoids the use of adapters, which can be misplaced. The resulting connector, although larger than a conventional single-configuration connector, can be surprisingly compact.

In general, the invention features a multi-configuration electrical connector for use in making electrical connections between an external defibrillator and defibrillation electrodes applied to a patient. The multi-configuration connector comprises a connector body; at least first and second pairs of electrical terminal elements supported in the connector body; and a pair of electrical conductors within the connector body, each conductor of the pair being configured to be electrically connected to one of the electrical terminal elements in each of the first and second pairs of electrical terminal elements, wherein the connector body and first and second pairs of electrical terminal elements are configured so that the multi-configuration connector is able to mate alternatively with first and second mating defibrillation electrode connectors, with the first pair of electrical terminal elements in electrical contact with mating electrical elements of the first mating defibrillation connector when the multi-configuration connector is mated with the first mating defibrillation connector, and with the second pair of electrical terminal elements in electrical contact with mating electrical elements of the second mating defibrillation connector when the multi-configuration connector is mated with the second mating defibrillation connector.

In another aspect, the invention features a multi-configuration electrical connector for use in making electrical connections between an external defibrillator and defibrillation electrodes applied to a patient. The multi-configuration connector comprising a connector body; at least first and second defibrillation electrode connectors integral with the connector body; wherein the connector body and first and second defibrillation electrode connectors are configured so that the multi-configuration connector is able to mate alternatively with at least a first and second mating defibrillation electrode connector.

Preferred implementations of the invention may incorporate one or more of the following. Each of the first and second incompatible defibrillation electrode connectors may comprise a pair of electrical terminal elements and the pair of electrical terminal elements may be configured to be in electrical contact with a pair of mating electrical elements in one of the mating defibrillation electrode connectors. The electrical terminal elements may comprise electrical pins. The multi-configuration electrical connector may further comprise a third pair of electrical terminal elements supported in the connector body, and each conductor of the pair of conductors may be configured to be electrically connected to one of the electrical terminal elements in each of the first, second, and third pairs of electrical terminal elements, and the connector body and the first, second, and third pairs of electrical terminal elements may be configured so that the multi-configuration connector is able to mate alternatively with first, second, and third mating defibrillation electrode connectors, with the third pair of electrical terminal elements in electrical contact with mating electrical elements of the first mating defibrillation connector when the multi-configuration connector is mated with the third mating defibrillation connector. The multi-configuration electrical connector may further comprise a third defibrillation electrode connector integral with the connector body, and the connector body and the first, second, and third defibrillation electrode connectors may be configured so that the multi-configuration connector is able to mate alternatively with a first, second, and third mating defibrillation electrode connector. The conductors of the pair of conductors may be configured to be electrically connected to only the pair of electrical terminal elements that is mated with a mating defibrillation connector, with the other electrical terminal elements electrically isolated from the pair of conductors. The multi-configuration connector may be configured so that only the defibrillation electrode connector that is mated with a mating defibrillation electrode connector is electrically live and the other defibrillation electrode connectors are electrically isolated. An associated pair of the electrical terminal elements may move into electrical contact with the conductors in response to the multi-function electrical connector being mated with a mating defibrillation connector. The multi-configuration electrical connector may further comprise one or more spring elements configured to return the electrical terminal elements to a position in which they are electrically isolated when not mated with a mating electrical connector. The multi-configuration electrical connector may be connected to a cable that is connected to a pair of defibrillation electrodes, whereby the same pair of defibrillation electrodes can be electrically connected to defibrillators with different mating electrical connectors. The multi-configuration electrical connector may be connected to a cable that is connected to a pair of defibrillation electrodes, whereby the same pair of defibrillation electrodes can be electrically connected to defibrillators with different mating electrical connectors. The multi-configuration electrical connector may further comprise one or more latch elements for retaining a mating defibrillation connector. The plurality of pairs of electrical terminal elements may be positioned so that all of the electrical terminal elements lie approximately in the same plane. The plurality of pairs of electrical terminal elements may be positioned so that each pair of electrical terminal elements is stacked on top of another pair of electrical terminal element.

The invention has many advantages (some of which may be achieved only in some implementations). For example, the multi-configuration connector can be configured so that unused electrical terminal elements are electrically isolated, thus avoiding harmful arcing that might occur between such elements.

Other features and advantages of the invention will be apparent from the detailed description, drawings, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
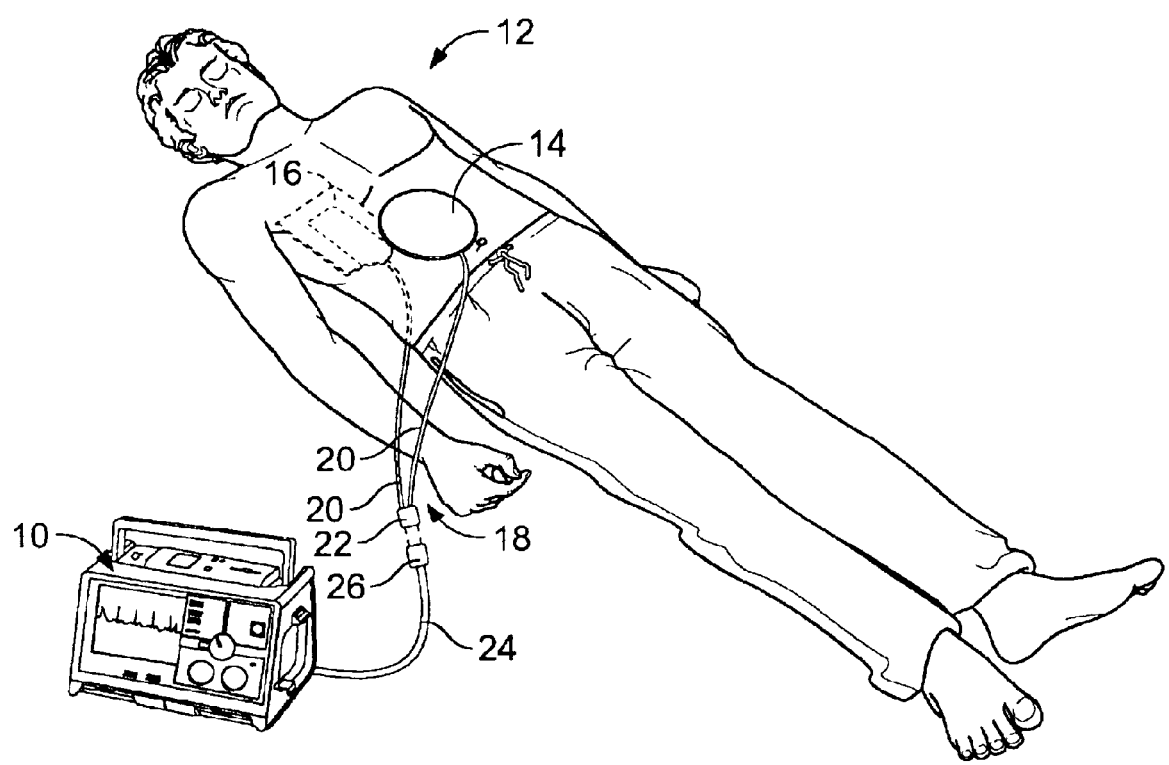
FIG. 1 is a diagrammatic, perspective view of a prior art external defibrillator and electrodes applied to a patient.
Figure 2:
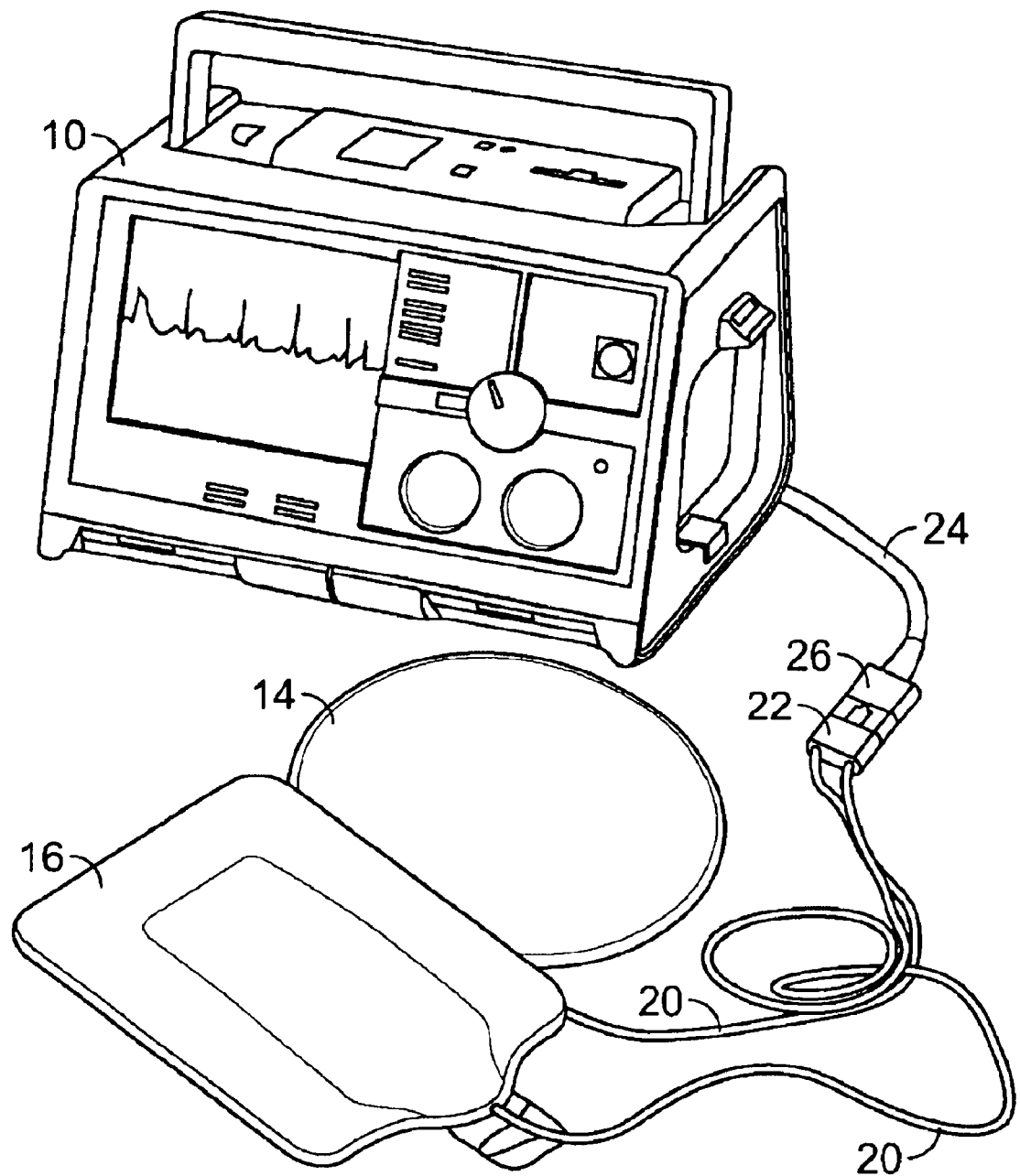
FIG. 2 is a perspective view of a prior art external defibrillator and preconnected electrodes.

The descriptions below are more than sufficient for one skilled in the art to construct the disclosed implementations. Unless otherwise mentioned, the processes and manufacturing methods referred to are ones known by those working in the art As shown diagrammatically in FIG. 1, an external defibrillator 10 delivers a defibrillation pulse to a patient 12 through a pair of chest electrodes 14, 16. The electrodes are connected to the defibrillator by a cable, which is typically divided into two parts, a patient cable 18, with a wire 20 extending from each electrode to a patient connector 22, and a defibrillator cable 24 extending from the defibrillator 10 to a defibrillator connector 26 that mates with the patient connector 22. The patient connector 22 and defibrillator connector 26 are shown disconnected in the figure. FIG. 2 shows the two electrodes 14, 16 preconnected to the defibrillator 10 before being applied to a patient. In this figure, the patient connector 22 and defibrillator connector 26 are shown connected.

Figure 3:
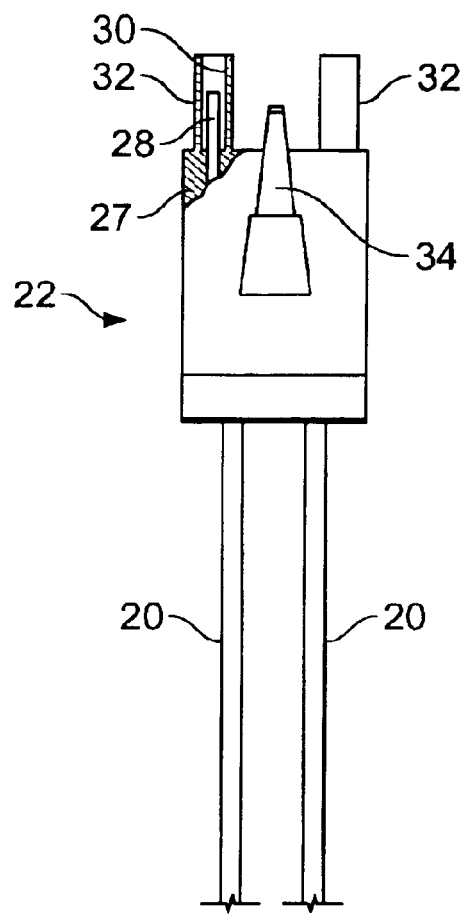
FIG. 3 is a plan view, partially cross-sectioned, of a prior art patient connector.

A typical patient connector 22 is shown in FIG. 3. The connector has a molded polymer body 27, into which wires 20 from the electrodes extend. Internally within the molded body the wires 20 are electrically connected to electrical pins 28 (one of which is shown in the partially cross-sectioned portion of the drawings). Each of the electrical pins protrudes into an elongated bore 30 of one of the protrusions 32. Each of the bores 30 is sized to receive a mating electrical pin or terminal (not shown) on the defibrillator connector. Each of the mating pins or terminals in the defibrillator connector engages one of pins 28 to complete the electrical circuit between the defibrillator and the electrodes. The polymer protrusions 32 are received in mating polymer cavities in the defibrillator connector. A latch element 34 positively engages a mating element on the defibrillator connector to prevent the two connectors from inadvertently pulling apart once they have been engaged.

The connector shown in FIGS. 2 and 3 is typical of the type sold by the assignee, ZOLL Medical Corporation, in 2003. At this time, other manufacturers of external defibrillators used the same general arrangement of electrodes, patient cable, patient connector, defibrillator connector, and defibrillator cable as shown in FIGS. 1 and 2. But the specific connector sold by other manufacturers differs from that shown in FIGS. 2 and 3. The result is that each manufacturer's electrodes cannot be connected to another manufacturer's defibrillator.

Figure 4:
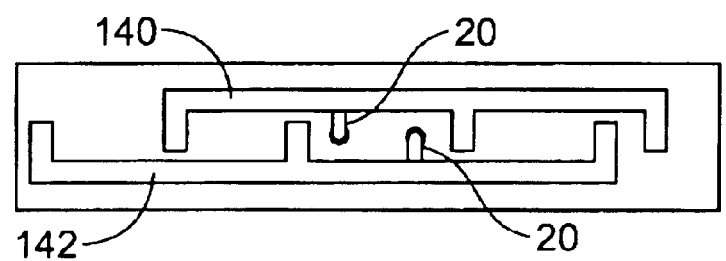
FIG. 4 is a cross-sectional view along 4—4 in FIG. 5.
Figure 5:
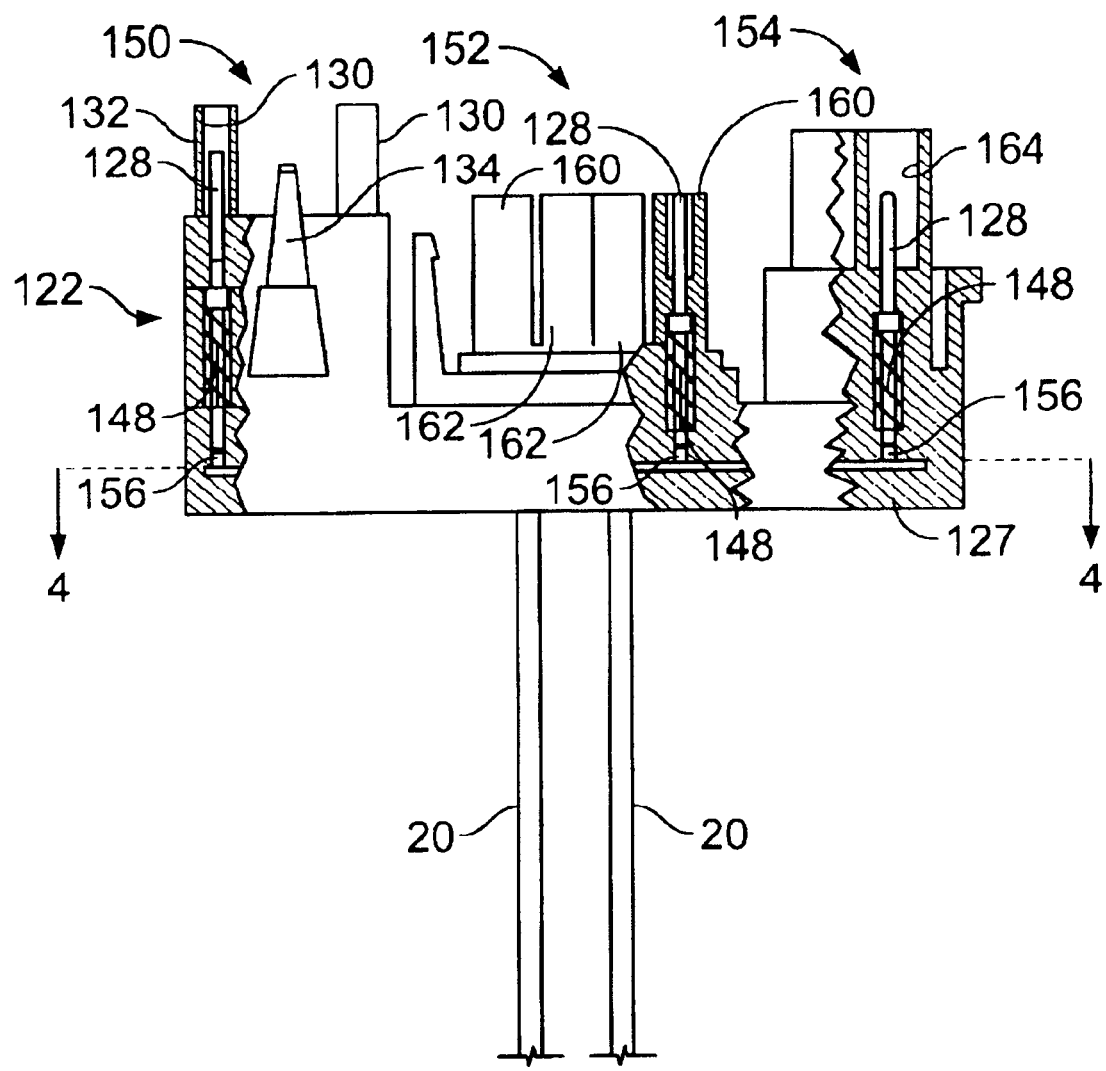
FIG. 5 is a plan view, partially cross-sectioned, of one implementation of the invention.

One implementation of the invention is shown in FIGS. 4 and 5. A patient connector 122 has a molded polymer body 127, into which wires 20 from the electrodes extend. Each wire is connected internally to one of two conductive bus bars 140, 142, which connect electrically to three different connectors 150, 152, 156, each supported in the connector body 127. Each connector 150, 152, 154 includes a pair of spring-loaded pins 128. When a mating defibrillator connector is plugged into one of the three connectors, the pins of that connector are forced inward into electrical contact with the bus bars 140, 142. Spring 148 urges the pins away from the bus bars, thereby keeping the pins of the unused connectors electrically isolated from the bus bars; this prevents electrical current from flowing to the unused pins and causing harm to a user. Gap 156 separating each pin from the bus bar provides the electrical isolation. A latch element 134 is provided at each connector to engage a mating element on the defibrillator connector to prevent the two connectors from inadvertently pulling apart once they have been engaged.

Connector 150 (including electrical pins 128, elongated bores, 130, protrusions 132, and latch element 134) resembles the standalone ZOLL Medical patient connector discussed above, and is configured to mate with a ZOLL Medical defibrillator connector.

Connector 152 resembles a standard Medtronic Physio-Control patient connector. The two electrical pins 128 are located in the outboard protrusions 160 (one of which is partially cross sectioned). The center two protrusions 162 are not used in the implementation shown, but could provide additional electrical connections to the electrodes.

Connector 154 resembles a standard Philips patient connector. The two electrical pins 128 are located in bores 164, which receive mating protrusions in a standard Philips defibrillator connector.

Many other implementations of the invention other than those described above are within the invention, which is defined by the following claims. A small number of the possible variations include the following. Many other configurations of cables and connectors are possible.

Instead of locating the multiple connectors on the patient connector (so that they are part of the electrode, and enable an electrode to be connected to any of a plurality of defibrillators), the multiple connectors could be located on the defibrillator connector (so that they are part of the defibrillator, and enable a defibrillator to be connected to any of a plurality of electrodes).

The patient cable could be eliminated by having the defibrillator connector plug into a patient connector located at the electrode, or the defibrillator cable could be eliminated by locating the defibrillator connector directly on the defibrillator and having the patient cable run all the way from the electrode to the defibrillator.

Different numbers of connectors could be combined. E.g., two connectors instead of three would provide some of the benefits of the invention.

The connectors could be arranged differently than the inline arrangement shown in FIGS. 4–5. E.g., instead of the short dimensions abutting other connector shapes, the wide dimensions of the connectors could abut, to produce a thicker connector body than shown. This would not have some of the packaging advantages of the inline configuration (e.g., that the connector will fit inside an electrode package), but it would still have some advantages of the invention. Instead of arranging the plurality of connectors in the inline configuration, the connectors could be supported in a turret, which is turned to select the active connector.

Many other arrangements could be provided for achieving electrical isolation of the unused connectors. E.g., instead of providing movable pins (so that the pins move upon insertion of a mating defibrillator connector, and unused pins remain spaced away from the bus bars), the pins could be stationary, and the other elements of the connector could move to achieve connection in the active connector and isolation in the unused connector.

While there are safety advantages to having the unused connector pins isolated electrically, some benefits of the invention could be had even if such electrical isolation was not provided (e.g., if wires 20 were permanently connected to the pins 128 of all three connectors in the implementation of FIGS. 4–5).

Latch elements such as elements 134, while preferable, are not necessary.

What is claimed is:

1. A multi-configuration electrical connector for use in making electrical connections between an external defibrillator and defibrillation electrodes applied to a patient, the multi-configuration connector comprising:

a connector body;

at least first and second pairs of electrical terminal elements supported in the connector body; and a pair of electrical conductors within the connector body, each conductor of the pair being configured to be electrically connected to one of the electrical terminal elements in each of the first and second pairs of electrical terminal elements, wherein the connector body and first and second pairs of electrical terminal elements are configured so that the multi-configuration connector is able to mate alternatively with first and second mating defibrillation electrode connectors, with the first pair of electrical terminal elements in electrical contact with mating electrical elements of the first mating defibrillation connector when the multi-configuration connector is mated with the first mating defibrillation connector, and with the second pair of electrical terminal elements in electrical contact with mating electrical elements of the second mating defibrillation connector when the multi-configuration connector is mated with the second mating defibrillation connector.

2. The multi-configuration electrical connector of claim 1 wherein the electrical terminal elements comprise electrical pins.

3. The multi-configuration electrical connector of claim 1 further comprising a third pair of electrical terminal elements supported in the connector body, and wherein each conductor of the pair of conductors is configured to be electrically connected to one of the electrical terminal elements in each of the first, second, and third pairs of electrical terminal elements, and wherein the connector body and the first, second, and third pairs of electrical terminal elements are configured so that the multi-configuration connector is able to mate alternatively with first, second, and third mating defibrillation electrode connectors, with the third pair of electrical terminal elements in electrical contact with mating electrical elements of the first mating defibrillation connector when the multi-configuration connector is mated with the third mating defibrillation connector.

4. The multi-configuration electrical connector of claim 1 or 3 wherein the conductors of the pair of conductors are configured to be electrically connected to only the pair of electrical terminal elements that is mated with a mating defibrillation connector, with the other electrical terminal elements electrically isolated from the pair of conductors.

5. The multi-configuration electrical connector of claim 4 wherein an associated pair of the electrical terminal elements move into electrical contact with the conductors in response to the multi-function electrical connector being mated with a mating defibrillation connector.

6. The multi-configuration electrical connector of claim 5 further comprising one or more spring elements configured to return the electrical terminal elements to a position in which they are electrically isolated when not mated with a mating electrical connector.

7. The multi-configuration electrical connector of claim 4 wherein the multi-configuration electrical connector is connected to a cable that is connected to a pair of defibrillation electrodes, whereby the same pair of defibrillation electrodes can be electrically connected to defibrillators with different mating electrical connectors.

8. The multi-configuration electrical connector of claim 1 or 5 wherein the multi-configuration electrical connector is connected to a cable that is connected to a pair of defibrillation electrodes, whereby the same pair of defibrillation electrodes can be electrically connected to defibrillators with different mating electrical connectors.

9. The multi-configuration electrical connector of claim 1 further comprising one or more latch elements for retaining a mating defibrillation connector.

10. The multi-configuration electrical connector of claim 1 wherein the plurality of pairs of electrical terminal elements are positioned so that all of the electrical terminal elements lie approximately in the same plane.

11. The multi-configuration electrical connector of claim 1 wherein the plurality of pairs of electrical terminal elements are positioned so that each pair of electrical terminal elements is stacked on top of another pair of electrical terminal element.

* * * * *

UNITED STATES PATENT AND TRADEMARK OFFICE
CERTIFICATE OF CORRECTION

PATENT NO.     : 6,961,611 B2
DATED          : November 1, 2005
INVENTOR(S)    : Michael R. Dupelle It is certified that error appears in the above-identified patent and that said Letters Patent is hereby corrected as shown below:

Column 2,
Line 61, "element" should be -- elements --.

Column 3,
Line 30, after "art" insert a -- . -- period.

Column 4,
Line 27, after "bores" delete the "," comma.

Column 6,
Line 37, "or 5" should be -- or 3 --.
Line 53, "element" should be -- elements --.

Signed and Sealed this

Sixth Day of June, 2006

JON W. DUDAS
*Director of the United States Patent and Trademark Office*